United States Patent [19]

Lifton

[11] Patent Number: 4,502,478
[45] Date of Patent: Mar. 5, 1985

[54] MEDICAL INSTRUMENT MOUTH GUARD

[76] Inventor: Lester J. Lifton, 5270 Strathmore Dr., Mechanicsburg, Pa. 17055

[21] Appl. No.: 481,978

[22] Filed: Apr. 4, 1983

[51] Int. Cl.³ ............................................. A61F 5/56
[52] U.S. Cl. ................................................... 128/136
[58] Field of Search ...................... 128/136, DIG. 26

[56] References Cited

U.S. PATENT DOCUMENTS 2,669,988  2/1954  Carpenter ........................... 128/136
4,351,331  9/1982  Gereg ........................... 128/DIG. 26

Primary Examiner—John D. Yasko
Attorney, Agent, or Firm—Millen & White

[57] ABSTRACT

A guard for use in a patient's mouth provides means for maintaining a patient's teeth spaced at a fixed minimum distance from each other. A passageway is provided for a medical instrument, such as an endoscope to be passed into the patient's oral cavity without contacting the patient's teeth. In a preferred aspect, an opening is also provided for an operator's fingers to safely facilitate manipulation of the medical instrument. The guard is held in place by a band around the patient's head.

18 Claims, 9 Drawing Figures

MEDICAL INSTRUMENT MOUTH GUARD

BACKGROUND OF THE INVENTION

This invention relates to a mouth guard for protecting medical instruments and fingers inserted in a patient's mouth from damage caused by the patient's teeth. More particularly, the invention in a preferred aspect relates to a mouth guard for use in connection with an endoscope and endoscopic procedures.

U.S. Pat. No. 3,513,838 discloses a teeth protector designed to protect teeth from chipping or breaking when instruments are inserted in a patient's mouth. The teeth protector comprises a pair of identical sections which allows a patient to move the jaw into biting contact with an instrument such as a laryngoscope placed in the patient's mouth. However, no provision is made for preventing damage to such instruments or for manipulating instruments placed in a patient's mouth. This device provides in fact that excessive pressures can be generated on the instrument.

U.S. Pat. Nos. 4,275,725 and 4,262,666 also disclose devices adapted for use in combination with instruments, such as a tube, to be inserted into a patient's mouth. However, both of these devices permit direct contact between the patient's teeth and the instrument with no means provided for protecting the instrument or for manipulation of the instrument in the patient's mouth.

Other known protective mouthpiece type devices include U.S. Pat. Nos. 3,139,088 and 3,682,164. However, like the above-discussed patents, the devices disclosed therein also fail to provide the features of protecting instruments and fingers placed in a patient's mouth from being bitten as well as failing to provide for ease of manipulation of the the instrument.

It is an object of the present invention to provide a mouth guard for mounting in a patient's mouth which permits insertion of medical instruments into the patient's mouth without risking damage to the instruments as a result of the patient biting them.

It is another object of the present invention to provide such a guard which also facilitates entry of and protection of fingers inserted in the patient's mouth for manipulation of the instrument.

Still another object is to provide such a guard which is adapted for being secured in the patient's mouth to prevent its inadvertent removal therefrom.

Another object is to provide such a guard which is made of a resilient material which allows the patient's teeth to make an impression therein without permanently deforming or breaking the guard, thereby preventing damage to patient's teeth.

Upon further study of the specification and appended claims, further objects and advantages of this invention will become apparent to those skilled in the art.

SUMMARY OF THE INVENTION

In accordance with the invention there is provided a guard comprising a main body or shield shaped for following the contour of the outside of a patient's mouth. A projection extends from the main body, when in use, into the patient's mouth in such a way that the patient's teeth can rest on the projection so as to maintain a minimum fixed spacing between the upper and lower teeth. A passageway is provided extending through the main body and the projection to permit passage of an instrument, such as an endoscope, through the guard and into the patient's mouth while preventing contact with the patient's teeth.

In a preferred aspect, the guard also comprises a cutout in the main body to permit passage of a person's fingers, e.g., an endoscope operator, into the patient's mouth without endangering the fingers. Means are preferably provided for securing a band, or strap, at each side of the guard, and easily releasable at at least one end, whereby the band can be passed around the back of the patient's head for securing the guard in the patient's mouth.

In a more preferred aspect, the guard is manufactured of a plastic type material of the type which is resilient, thereby allowing the patient's teeth to impress thereon, while at the same time being rigid enough to resist permanent deformation. Furthermore, the material is such that the device can be manufactured by such conventional techniques as injection molding. The choice of material is conventional and well known to those skilled. For example, one such material is a high density polyethylene resin, sold by USI Chemicals under the tradename PETROTHENE.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DISCUSSION OF THE INVENTION

Figure 1:
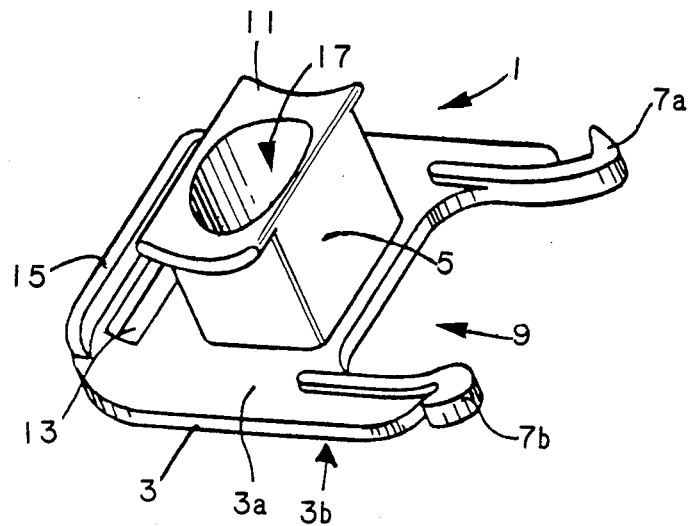
FIG. 1 is an isometric view, viewed from the rear, of the mouth guard according to the invention.
Figure 2:
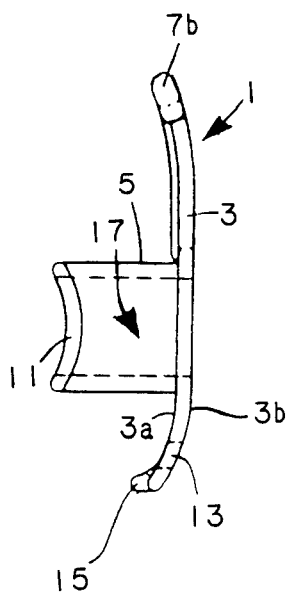
FIG. 2 is a bottom view of the guard in accordance with the invention.
Figure 3:
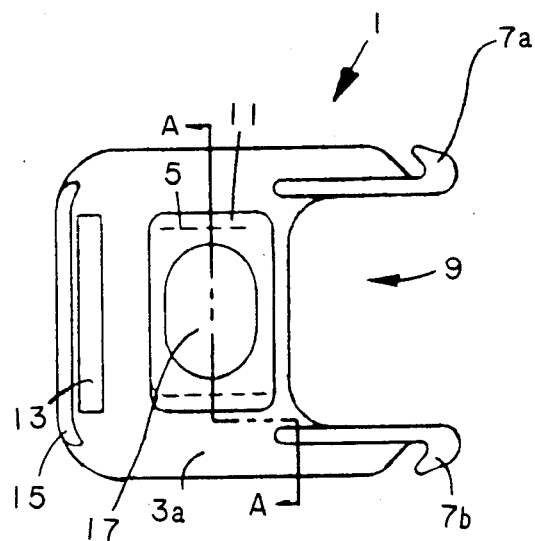
FIG. 3 is a rear plan view of the guard according to the invention.
Figure 4:
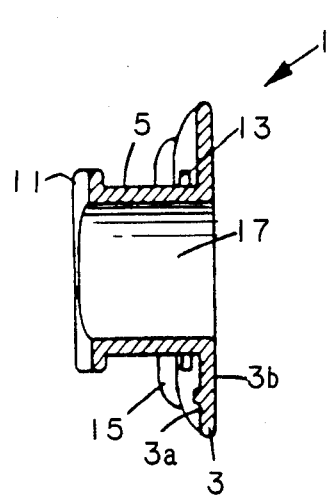
FIG. 4 is a cross-section view along line AA of FIG. 3.

FIG. 1 is a view generally from the rear of the guard 1 of the invention generally showing most of its features. More specifically, the main body 3 is shown having a rear wall 3a and a front wall 3b. As better shown in FIG. 2, the main body 3 is generally shaped to follow the curvature of a patient's face around the mouth area.

The main body 3 also includes a hollow generally rectilinear projection 5, preferably approximating the general shape of a tube, but with its upper and lower outside surfaces being generally flat so that when used by a patient, the teeth of the patient can rest comfortably thereon.

The end of the projection 5 furthest from the rear wall 3a of the main body 3 includes a ridge 11 at the upper and lower portions so that if any sliding forward of the projection 5 against the patient's teeth occur after the guard is placed in the patient's mouth, the ridges 11 will abut against the back of the patient's teeth and prevent the guard from sliding out of the patient's mouth.

Thus, in use the rear wall 3a will rest against the outside of the patient's mouth. The patient's teeth will rest on projection 5 at a minimum fixed spacing defined by the height of the projection, with the teeth being prevented from sliding off the guard by ridges 11 at the end of the projection 5. A second ridge-like portion 15 which rests against the patient's left cheek region serves to reinforce or provide extra support to the guard at a cutout 13 to which will be attached a securing strap.

In a preferred embodiment the guard 1 is designed as a guard adapted for use with an endoscope. In this case an opening 17 is provided extending through the projection 5 and main body 1 all the way through the device so that when in use, access for an endoscope can be provided from the outside into the patient's mouth without the endoscope coming in contact with the teeth. As discussed above, the opening or passageway 17 is shaped so as to accommodate an endoscope passed therethrough.

In order to further facilitate guiding or positioning of an instrument, such as an endoscope, through passageway 17 into, e.g., the posterior pharynx of the patient, a cutout 9 is provided in the main body 3, preferably on the left side when viewed from the front, to permit the, e.g., endoscopist, to safely manipulate the instrument, without danger of being bitten. The cutout portion 9 divides the left side of the main body 3 into two prongs 7a and 7b and is defined thereby.

Figure 5:
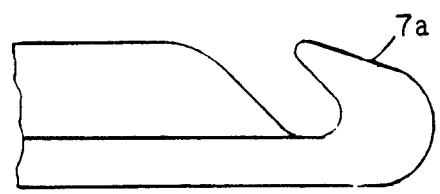
FIG. 5 is an enlarged partial view of the band engaging portion of the guard as sown circled in FIG. 3.

In a preferred aspect, the projections are shaped as engaging hooks 7a and 7b as shown enlarged in FIG. 5. These projections, like the cutout 13, are reinforced against breaking when a securing strap is attached thereto. On the other side of the main body is provided the cutout 13. This construction permits use of the guard 1 with a preferably elastic headband 21 which is appropriately shaped for engaging in a resistably detachable manner with the cutout 13, and for easily engaging and disengaging from the prongs 7a and 7b.

Figure 6:
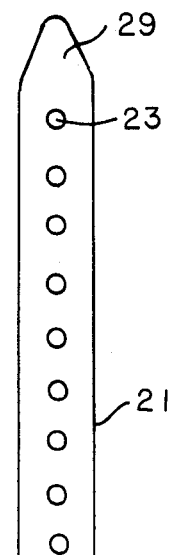
FIG. 6 is a view of a head band adapted for use in conjunction with the guard according to the invention.
Figure 7A:
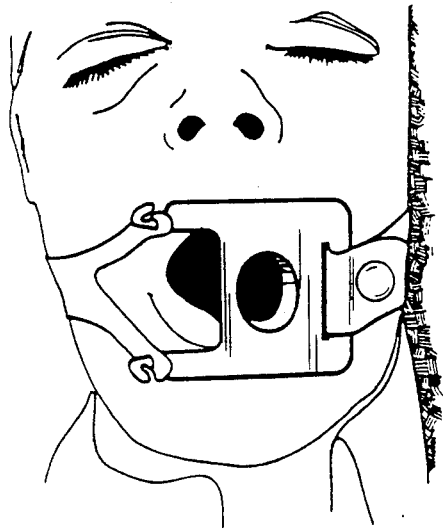
FIGS. 7A, 7B and 7C are respective views of the guard in position with the securing band and showing the attaching button on one end, the guard in position while an endoscope is being positioned in the patient, and the guard while conducting endoscopic procedures.
Figure 7B:
Figure 7C:
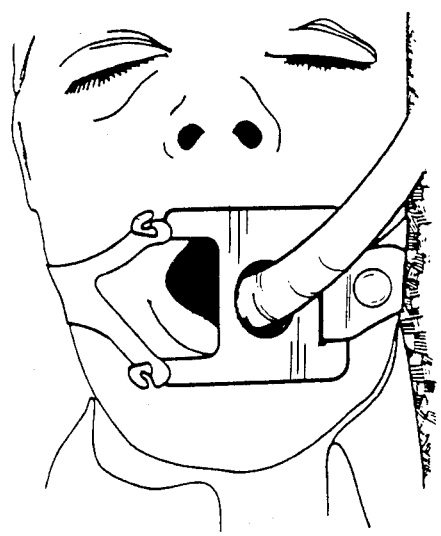

Thus, in use the end 29 of band or strap 21 shown in FIG. 6 can be passed through cutout passageway and folded over so that two of the holes 23 align and a fastener, e.g., a button, can be passed through the two openings to ensure attachment at the cutout passageway 13 end. Thereby, when in use the guard 1 is secured on a patient by placing in the patient's mouth and passing the band or strap 21 around the back of the patient's head. The other end 27 of the band is divided into two parts 27a and 2b having holes 25a and 25b through which the ends 27a and 27b can be engaged with the prongs 7a and 7b.

With respect to the construction of the guard 1 it is preferred that it be a single piece integral unit, i.e., the projection 5 and prongs 7a, 7b, etc., are part of the same piece making up the main body 3. More preferably, the guard 1 is made of a plastic material which is resilient but rigid and non-brittle, e.g., as previously discussed, the material can be a high density polyethylene resin. Such a material permits a patient's teeth to make an impression in the material yet not bend, crack or break it. Moreover, such a material provides additional protection for patients' teeth when capped, or if they have prosthesis in place. An additional feature is that the material should be of the type that the guard 1 can be injection molded by conventional techniques, and as noted previously the selection of the material is conventional and known to those skilled in the art. For example, one such material could be the chemical marketed by USI Chemicals under the tradename PETROTHENE. Such a material is low-cost and would enable the guards 1 to be manufactured as one use disposable units.

Although the guard 1 is intended for single use, the band or strip 21 preferably is constructed for multiple use. For this purpose it is preferred that the band 21 be made of a material such as, for example, latex rubber.

Alternatively, the guard can be constructed for multiple uses. The selection of a material for constructing such a guard would also be conventional. However, it is preferred that the material is one that can be easily and readily sterilized without damage thereto for multiple uses.

Without further elaboration, it is believed that one skilled in the art can, using the preceding description, utilize the present invention to its fullest extent. The following preferred specific embodiment is, therefore, to be construed as merely illustrative, and not limitative of the remainder of the disclosure in any way whatsoever.

EXAMPLE

In an example of one construction especially adapted for use with patients, the main body of the guard 1 will generally follow a straight line in the vertical direction. The horizontal line, i.e., transverse across a patient's face, will follow a slight radius of curvature on the side having the cutout portion 9 while following a tighter curve or radius of curvature on the side opposite the cutout 9. This is because the cutout 9, to permit entry of the endoscopists' fingers into the patient's mouth, is made relatively large requiring that the projection 5 is off-center with respect to the main body 3. Thus, by making the curvature different on each side, the guard 1 will more closely follow the patient's face contour when in use.

The guard 1 itself is about 2 inches high in the vertical direction by about 2.6 inches wide in the horizontal or transverse direction. The projection 5 is about 1 inch in height and about 0.80 inches in width. Furthermore, at the end furthest from the main body 3, the lip or ridge 11 projects about 0.10 inches both at the top and bottom of the projection 5. The opening or passageway 17, to accommodate an endoscope is generally elliptical in shape and about 0.60 inches in width by 0.80 inches in height.

The band or strap 21 is about 18 inches long by 1 inch wide. The end portions 25a and 25b are 2 inches long with a ⅛ inch spacing between them, and the spacing between holes 23 is 1 inch to permit easy folding over and coupling.

The preceding example can be repeated with similar success by substituting the generically or specifically described reactants and/or operating conditions of this invention for those used in the preceding example.

Although this device of the invention is especially adapted for use with an endoscope, changes and modifications can be made in its construction to adapt it for use with other types of instruments requiring similar protection.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A protective mouth guard comprising:
   a main body shield having an inner face adapted for resting generally flush against a patient's face around the mouth;
   a projection extending from said inner face so as to extend into a patient's mouth a partial distance beyond the front teeth when in use, and having a shape for maintaining the patient's teeth in spaced apart relationship and further comprising a passageway extending therethrough and through said main body shield for providing passage to a medical instrument from the exterior into the patient's oral cavity while preventing contact between the patient's teeth and the medical instrument when in use; and
   said main body shield having, on one side of the projection, an open portion defined by two prongs and large enough to permit entry of an operator's fingers into the patient's oral cavity, when the guard is positioned therein, for facilitating manipulation of an instrument passed through said projection passageway and into the patient's oral cavity, and main body shield further having a cutout portion on the side of the projection opposite the open portion defined by said two prongs.

2. A guard as in claim 1, further comprising, in combination, a strap adapted for engaging the main body at said cutout portion, for being passed around a patient's head, and for engaging the prong projections for securing the guard in a patient's mouth when in use.

3. A guard as in claim 1, wherein said guard is a one-piece integral unit.

4. A guard as in claim 2, wherein said guard is a one-piece integral unit.

5. A guard as in claim 3, wherein said guard is made of a generally resilient, rigid, non-brittle plastic material, with said guard having been manufactured by an injection molding technique.

6. A guard as in claim 4, wherein said guard is made of a generally resilient, rigid, non-brittle plastic material, with said guard having been manufactured by an injection molding technique.

7. A guard as in claim 2, wherein said strap is made of latex rubber.

8. A guard as in claim 1, wherein said passageway is of a size sufficient to accommodate an endoscope.

9. A guard as in claim 1, wherein said projection comprises ridges at the top and bottom thereof at the end spaced from the main body shield for abutting against the rear of a patient's teeth and preventing the guard from sliding out of the patient's mouth.

10. A protective mouth guard comprising:
    a main body shield having an inner face adapted for resting generally flush against a patient's face around the mouth;
    a projection extending from said inner face so as to extend into a patient's mouth a partial distance beyond the front teeth when in use, and having a shape for maintaining the patient's teeth in spaced apart relationship and further comprising a passageway extending therethrough and through said main body shield for providing passage to a medical instrument from the exterior into the patient's oral cavity while preventing contact between the patient's teeth and the medical instrument when in use; and
    said main body shield having, on one side of the projection, an open portion defined by two prongs and large enough to permit entry of an operator's fingers into the patient's oral cavity, when the guard is positioned therein, for facilitating manipulation of an instrument passed through said projection passageway and into the patient's oral cavity, and main body shield further having strap engaging means on the side of the projection opposite the open portion to permit the engaging thereon of the end of a strap to be fastened around the patient's head for holding said mouth guard in place.

11. A guard as in claim 10 further comprising, in combination, a strap adapted for engaging the main body at said strap engaging means, for being passed around a patient's head, and for engaging the prong projections for securing the guard in the patient's mouth when in use.

12. A guard as in claim 10, wherein said passageway is of a size sufficient to accommodate an endoscope.

13. A guard as in claim 10, wherein said projection comprises ridges at the top and bottom thereof at the end spaced from the main body shield for abutting against the rear of a patient's teeth and preventing the guard from sliding out of the patient's mouth.

14. A guard as in claim 10 wherein said guard is a one-piece integral unit.

15. A guard as in claim 11, wherein said guard is a one-piece integral unit.

16. A guard as in claim 15, wherein said guard is made of a generally resilient, rigid, non-brittle plastic material, with said guard having been manufactured by an injection molding technique.

17. A guard as in claim 16, wherein said guard is made of a generally resilient, rigid, non-brittle plastic material, with said guard having been manufactured by an injection molding technique.

18. A guard as in claim 11, wherein said strap is made of latex rubber.

* * * * *